(12) United States Patent
Bouvier et al.

(10) Patent No.: US 8,735,643 B2
(45) Date of Patent: May 27, 2014

(54) AGGREGATE ZEOLITIC ABSORBENTS, THEIR METHOD OF PREPARATION AND THEIR USES

(75) Inventors: Ludivine Bouvier, Billere (FR); Stéphane Kieger, Sartrouville (FR); Catherine Laroche, Vernaison (FR); Philibert Leflaive, Mions (FR); Tom Frising, Lyons (FR)

(73) Assignees: Cece S.A., La Garenne Colombes (FR); Institut Francais du Petrole, Rueil Malmamaison (FR)

( * ) Notice: Subject to any disclaimer, the term of this patent is extended or adjusted under 35 U.S.C. 154(b) by 830 days.

(21) Appl. No.: 12/808,072

(22) PCT Filed: Dec. 16, 2008

(86) PCT No.: PCT/FR2008/052316
§ 371 (c)(1),
(2), (4) Date: Feb. 1, 2011

(87) PCT Pub. No.: WO2009/081023
PCT Pub. Date: Jul. 2, 2009

(65) Prior Publication Data
US 2011/0184165 A1    Jul. 28, 2011

(30) Foreign Application Priority Data
Dec. 20, 2007   (FR) ..................... 07 60088

(51) Int. Cl.
*C07C 7/13* (2006.01)
*B01J 29/06* (2006.01)
*B01J 20/00* (2006.01)

(52) U.S. Cl.
USPC ........... 585/820; 585/826; 585/828; 585/831; 423/700; 423/713; 502/64; 502/67; 502/69; 502/73; 502/79; 502/407; 502/414

(58) Field of Classification Search
USPC .................. 502/64, 67, 69, 73, 79, 407, 414; 423/700, 713; 585/820, 826, 828, 831; 536/127; 568/700, 758
See application file for complete search history.

(56) References Cited

U.S. PATENT DOCUMENTS

| | | | |
|---|---|---|---|
| 6,410,815 B1 * | 6/2002 | Plee et al. | ...................... 585/828 |
| 2005/0170947 A1 * | 8/2005 | Plee et al. | ........................ 502/64 |

OTHER PUBLICATIONS

Warzywoda, J. et al., "Characterization of zeolites A and X Grown in low earth orbit." Journal of Crystal Growth, 220 (2000), pp. 150-160.
Khemthong, P. et al., "Systhesis and Characterization of Zeolite LSX from Rice Husk Silica." Suranaree J. Science Technology, (2007) 13(4), pp. 367-379.
Robson, H. et al., "Verified Syntheses of Zeolitic Materials," Second Revised Edition, Published on behalf of the Synthesis Commission of the International Zeolite Association by Elsevier, (2000), pp. 150-155.

* cited by examiner

*Primary Examiner* — Elizabeth Wood
(74) *Attorney, Agent, or Firm* — McDonnell Boehnen Hulbert & Berghoff LLP

(57) ABSTRACT

The invention relates to aggregate zeolitic adsorbents based on faujasite X type zeolite powder having a low silica content and small crystals, exchanged with barium or based on faujasite X type zeolite having a low silica content and small crystals, exchanged with barium and potassium.
The invention also relates to the method for preparing said aggregate zeolitic adsorbents, and also their uses for separating sugars, polyhydric alcohols, isomers of substituted toluene, cresols, or for recovering very high purity paraxylene.

29 Claims, No Drawings

AGGREGATE ZEOLITIC ABSORBENTS, THEIR METHOD OF PREPARATION AND THEIR USES

The invention relates to aggregate zeolitic adsorbents based on faujasite X type zeolite powder having a low silica content and small crystals, exchanged with barium or based on faujasite X type zeolite having a low silica content and small crystals, exchanged with barium and potassium.

These adsorbents may be used more particularly for producing highly pure paraxylene, from an aromatic hydrocarbon feedstock containing isomers with eight carbon atoms.

The prior art has recognized that the adsorbents consisting of X or Y zeolites exchanged by means of ions such as barium, potassium or strontium, alone or in a mixture, are effective for selectively adsorbing paraxylene from a mixture of aromatic hydrocarbons.

U.S. Pat. No. 3,558,730, U.S. Pat. No. 3,558,732, U.S. Pat. No. 3,626,020 and U.S. Pat. No. 3,663,638 show that adsorbents comprising aluminosilicates exchanged with barium or potassium or with barium alone (U.S. Pat. No. 3,960,774) effectively separate paraxylene from a mixture of aromatic isomers with 8 carbon atoms ($C_8$).

A method for preparing these adsorbents is described for example in U.S. Pat. No. 3,878,127 and consists in treating, in hot caustic soda, aggregates (zeolite X+binder) having a $Na_2O/Al2O_3$ ratio that is strictly lower than 0.7 in order to replace the exchangeable cations of the zeolite (such as the protons or cations of group IIA), by sodium prior to an exchange with barium and/or barium+potassium, the prior exchange with sodium enabling a larger quantity of barium or barium plus potassium ions to be added to the zeolitic structure.

These adsorbents are used as adsorption agents in liquid phase processes, preferably of the simulated countercurrent type, similar to those described in U.S. Pat. No. 2,985,589, which apply to aromatic $C_8$ cuts, among others.

The zeolites encountered in the prior art for separating xylenes belong to the structural type of faujasite, first described in U.S. Pat. No. 2,882,244 and U.S. Pat. No. 3,130,007, which are crystallized aluminosilicates having cages with perfectly defined size, connected in the three dimensions.

U.S. Pat. No. 6,884,918 recommends a faujasite X with a Si/Al atomic ratio of between 1.15 and 1.5. U.S. Pat. No. 6,410,815 teaches that zeolitic adsorbents like those described in the prior art, but for which the faujasite has a low silica content and has a Si/Al atomic ratio close to 1 (which we shall call LSX, an abbreviation of Low Silica X), are advantageously used for separating paraxylene.

In the references listed above, the zeolitic adsorbents are in the form of powder or in the form of aggregates mainly consisting of zeolite and up to 15 to 20% by weight of inert agglomeration binder.

Since LSX zeolites are usually synthesized by nucleation and crystallization of aluminosilicate gels, the powders produced are particularly difficult to use on the industrial scale (high pressure drops during handling operations), and the aggregate forms are preferred, for example in the form of granules or grains, which do not have the drawbacks inherent in powdery materials.

These aggregates, whether in plate, bead or extruded form, generally consist of a zeolite powder, which constitutes the active element (in the context of adsorption) and a binder for obtaining the cohesion of the crystals in the form of aggregates and for conferring thereon sufficient mechanical strength to withstand the vibrations and movements to which they are subjected during their processing.

These aggregates are prepared for example by pasting zeolite powder with a clay paste, in proportions of about 80 to 90% by weight of zeolite powder for 20 to 10% by weight of agglomeration binder, followed by shaping into bead, plate or extruded form, and heat treatment at high temperature for baking the clay and reactivating the zeolite, the barium exchange being carried out before and/or after the agglomeration of the zeolite powder with the agglomeration binder.

Zeolitic aggregates are obtained having a particle size distribution of a few millimeters in general, and which, if the choice of the binder and the granulation are carried out according to the rules of the art, have a set of satisfactory properties, in particular porosity, mechanical strength, and abrasion resistance.

However, the adsorption properties of these aggregates are obviously reduced in comparison with the initial active powder, due to the presence of inert agglomeration binder.

Various means have been proposed to overcome this drawback of the binder being inert with regard to the adsorbent performance, including the conversion of the binder, fully or partly, to zeolite or zeolitization. To perform this operation easily, use is made of zeolitizable binders belonging to the family of kaolinite, halloysite, kaolins and/or metakaolins, previously calcined at temperatures of between 500° C. and 700° C.

One alternative consists in molding the kaolin grains and then zeolitizing the kaolin; the principle thereof is described in "Zeolite Molecular Sieves" by D. W. Breck, John Wiley and Sons, New York, p 320 et seq". This technology has been applied successfully for obtaining grains of zeolite A or zeolite X, consisting of up to 95% by weight of the zeolite itself and a residue of unconverted binder (see for example U.S. Pat. No. 3,119,660 where the production of zeolite X is found to require the addition of a source of silica to the reaction medium).

U.S. Pat. No. 4,818,508 describes the preparation of aggregates based on zeolite A, X or Y by digestion of reactive clay preforms (obtained by heat treatment of unreactive clay—such as halloysite or kaolinite—whereof at least 50% by weight is in the form of particles having a particle size distribution between 1.5 µm and 15 µm), preferably in the presence of a pore forming agent and with an alkali metal oxide. The examples relative to the synthesis of aggregates based on zeolite X also show that it is necessary to add a source of silica, which is not the case in preparing aggregates based on zeolite A. However, this method does not make it possible in principle to control the size of the zeolite which is formed after digestion of the reactive clay.

JP 3 066 430 teaches the possibility of forming grains of zeolite X having a low Si/Al ratio, lower than 1.25, by mixing a zeolite LSX powder with a Si/Al ratio lower than 1.25 with kaolinite, potash, caustic soda and carboxymethylcellulose, followed by shaping by extrusion. The grains thus obtained are dried, calcined at 600° C. for two hours, and then immersed in a solution of caustic soda and caustic potash at 400° C. for 2 days.

However, the associated methods described in the preceding patents are cumbersome and have drawbacks, either the excessive reaction time, or the large number of steps involved. According to the inventors, it is also possible that the heat treatment as described and claimed in JP 3 066 430, after the shaping step, will contribute to the amorphization of the grains, and that the caustic digestion that follows is intended to recrystallize them, thereby explaining the slowness of the method.

U.S. Pat. No. 6,410,815 describes a method for fabricating aggregates of zeolite LSX having a Si/Al ratio such that $1 \leq Si/Al \leq 1.15$ exchanged with barium and optionally potassium, by agglomerating the zeolite LSX powder with a binder which may optionally be zeolitized by immersion of the aggregate in an alkaline liquor. After exchange of the ions of the zeolite with barium (and optionally potassium) ions and activation, the aggregates thus obtained have improved selectivities with regard to the paraxylene contained in the $C_8$ aromatic cuts consisting typically of paraxylene, metaxylene, orthoxylene, ethylbenzene, in comparison with adsorbents prepared from a zeolite X powder having a Si/Al ratio such that $1.15 < Si/Al \leq 1.5$.

Apart from the good selectivity properties with regard to the species to be separated from the reaction mixture, the adsorbent must have good mass transfer properties in order to guarantee a sufficient number of theoretical trays to carry out an efficient separation of this species in the mixture, as indicated by Ruthven in the work entitled "Principles of Adsorption and Adsorption Processes", pages 326 and 407. Ruthven states, on page 243, that in the case of an aggregate adsorbent, the total mass transfer depends on the addition of the intra-crystalline diffusional resistance and the diffusional resistance between the crystals. The intra-crystalline diffusional resistance is proportional to the square of the radii of the crystals and inversely proportional to the diffusivity of the intra-crystalline molecules. As to the diffusional resistance between the crystals (also called macroporous resistance), it is proportional to the square of the radii of the aggregates and inversely proportional to the diffusivity of the molecules in the macropores. For a zeolitic structure, a given aggregate size and operating temperature, the diffusivities are fixed and the only means to improve the mass transfer consists in reducing the diameter of the crystals. A gain in total transfer is thereby obtained, by reducing the size of the crystals.

To estimate this improvement in the transfer kinetics, use can be made of the theory of trays described by Ruthven in Principles of Adsorption and Adsorption Processes, chapter 8, pages 248-250. This approach is based on the representation of a column by a finite number of hypothetical ideally stirred reactors (theoretical stages). The equivalent height of a theoretical tray is a direct measurement of the axial dispersion and the mass transfer resistance of the system.

In the particular case of the purification of gases, the prior art (EP 1 105 213) has recognized that a reduction of the crystal size increased the adsorption capacity in dynamic operation and decreased the resistance to intra-crystalline diffusion. In this respect, EP 1 105 213 describes a method for fabricating molecular sieves to remove $CO_2$. This molecular sieve is formed by agglomerating a faujasite X powder having a low silica content (LSX) of which more than 97% of the cationic sites are occupied by sodium ions, with an inert binder, a distributing agent and a pore-forming agent. Among other factors, more than 80% of said LSX powder must consist of crystals having a size between 1 µm and 2 µm, in order to improve the dynamic $CO_2$ adsorption capacity and to reduce the resistance to intra-crystalline transfer.

A third property of the adsorbent required to guarantee good performance of the liquid phase separation method of the simulated countercurrent type is good mechanical strength. In fact, in standard operating conditions of this type of method, mechanical stress is applied to the adsorbent within the units, causing the formation of fines, leading to a deterioration of performance (*Primary analysis on state of xylene adsorption unit*, Li et al, Jingxi Shiyou Huagong, 4, (2004), particularly if the mechanical strength of the adsorbent is low.

The mechanical strength of adsorbents is characterized using a "BCS tester" apparatus sold by Vinci Technologies following the Shell method (supplied with the device) (Shell Method Series SMS1471-74 "Determination of Bulk Crushing Strength of Catalysts" Compression-Sieve Method), which serves to determine the crushing strength of a bed of solids (beads or extrudates having a length of 6 mm or shorter).

These tests show that, all other things remaining equal, an adsorbent has lower mechanical strength with lower crystal size.

It is known that aggregate zeolitic adsorbents based on zeolite LSX exchanged with barium (or barium+potassium) have good adsorption properties for xylenes, good selectivity for paraxylene in a liquid phase $C_8$ aromatic mixture.

It is also known that small zeolite crystals generally provide better mass transfer than crystals of the same zeolite having a larger size, particularly because of the improved mass transfer.

A person skilled in the art therefore expects aggregate zeolitic adsorbents based on zeolite LSX with small crystals and exchanged with barium (or barium+potassium) to have good paraxylene adsorption properties, good selectivity and good mass transfer, and hence that such adsorbents have good performance for separating paraxylene contained in a mixture of $C_8$ aromatics in a liquid phase method, for example of the simulated countercurrent type.

However, the inventors have found that zeolitic adsorbents based on zeolite LXS with small crystals agglomerated with a binder conventionally do not have good mechanical strength and that their separation performance for $C_8$ aromatic isomers and particularly xylenes deteriorates over time due to the formation of fines, and even faster as the size of the zeolite LSX crystals is lower.

It has now been discovered that it is possible to prepare zeolitic adsorbents from LSX zeolite crystals of small particle size, while retaining a high mechanical strength of the aggregates, and especially a satisfactory strength for separation applications especially for the separation of xylenes, in particular paraxylene.

The present invention relates to zeolitic adsorbents, usable in particular for separating paraxylene from a mixture of $C_8$ aromatic compounds, having excellent performance, particularly in terms of selectivity to paraxylene, adsorption capacity for xylene, mass transfer and mechanical strength, said adsorbents being particularly suitable for use in a liquid phase xylene separation method, preferably of the simulated countercurrent type.

More precisely, the aggregate zeolitic adsorbent according to the invention is based on LSX zeolite crystals having a mean number diameter of less than or equal to 4 µm, a Si/Al atomic ratio such that $(1.00 \pm 0.05) \leq Si/Al \leq 1.15$ and preferably a Si/Al atomic ratio=$1.00 \pm 0.05$, whereof at least 90% of the exchangeable cationic sites are occupied either by barium ions or by barium ions and potassium ions, characterized in that the mechanical strength measured by the Shell series SMS1417-74 method adapted to the aggregates having a size smaller than 1.6 mm is greater than or equal to 2 MPa.

The mechanical strength indicated above is measured using a "BCS tester" apparatus sold by Vinci Technologies, following the Shell series SMS1471-74 method, and adapted to the zeolitic aggregates having a size lower than 1.6 mm.

According to a preferred embodiment of the invention, the aggregate zeolitic adsorbent also has one or more of the following features, considered separately or in combination:

the aggregate zeolitic adsorbent comprises zeolite LSX powder having a Si/Al atomic ratio such that (1.00±0.05)≤Si/Al≤1.15, and preferably a Si/Al atomic ratio=1.00±0.05, of which values lower than 1 reflect the analytical uncertainties on the measurement of this ratio, and the higher values, either the same analytical uncertainty, or a tolerable deviation in purity of the product, exchanged to at least 90% with barium ions alone or with barium ions and potassium ions, the exchangeable sites occupied by potassium possibly accounting for up to ⅓ of the exchangeable sites occupied by the barium plus potassium ions (the optional complement is generally provided by alkali or alkaline-earth ions other than barium and potassium);

the aggregate zeolitic adsorbent comprises a binder that is inert to adsorption in a proportion of less than or equal to 20% by weight, preferably 15% by weight, of the total mass of aggregate;

the Dubinin volume of the aggregate zeolitic adsorbent, which is an estimate of the microporous volume measured by nitrogen adsorption at 77 K, is 0.200 cm$^3$/g, preferably greater than or equal to 0.220 cm$^3$/g, even more preferably greater than or equal to 0.225 cm$^3$/g.

The aggregate zeolitic adsorbents of the invention generally have a size distribution giving a mean diameter of between 0.3 mm and 1.6 mm.

The size distribution of the granules is measured by liquid laser granulometry using a Mastersizer 2000 apparatus.

The laser granulometry technique uses the principle of diffraction and diffusion of a laser beam (wavelength 466 and 633 nm) created by the passage of the granules into its optical field. It is based on the two basic theories of Fraunhofer and Mie.

The measurement of the size distribution of a sample on the Mastersizer 2000 comprises three steps:

The sample is first dispersed in deionized water until the required concentration is obtained, before being introduced into the optical bench;

the diffraction image of the sample is acquired on the optical bench by circulating the sample through a glass cell with parallel sides lit by a laser light beam (466 and 633 nm);

the raw data are analyzed with the Malvern software.

The result obtained is the particle size distribution where the x-axis (in μm) corresponds to the diameter of the granules and where the y-axis represents the volume percentage of each particle size class, a distribution from which the median volume diameter D (v, 0.5) can be deducted.

The Dubinin volume is calculated from the Dubinin-Radushkevich equation, as described by Lowell et al in "Characterization of Porous Solids and Powders: Surface Area, Pore Size and Density", chapter 9, "Micropore Analysis", pages 143-145:

$$\log V = \log V_0 - D\left(\log \frac{P}{P_0}\right)^2$$

which relates the volume V of nitrogen adsorbed on the adsorbent material at the gauge pressure $P/P_0$. The Dubinin volume is the volume $V_0$, maximum volume of nitrogen vapor that can be condensed in the micropores of the adsorbent material. It is expressed in cm$^3$ of nitrogen vapor (related to standard conditions) per gram of adsorbent.

The Dubinin volume is then calculated from the volume $V_0$ of gas, which is then converted to the volume of liquid; it is expressed in cm$^3$ per gram of adsorbent, and corresponds to the micropore volume available for adsorption.

Prior to the measurement, the sample is pretreated at 500° C. for 12 hours under vacuum (P<5.10$^{-6}$ Torr; or 6.7.10$^{-4}$ Pa). The measurement is then taken on a Micromeritics ASAP 2010 M type apparatus. The isotherm is plotted using a pressure table of at least 35 points between 0.01 and 1 $P/P_0$. The value of log V is plotted on a diagram as a function of $(\log(P/P_0))^2$. The Dubinin volume is obtained from the x-axis at the origin of the linear regression line of the points of which $(\log(P/P_0))^2$ is between 1 and 2 (or 0.039<$P/P_0$<0.1). The measurement uncertainty is ±0.003.

According to a preferred embodiment, the zeolite LSX of the aggregates according to the invention essentially consists of crystals having a mean (number) diameter measured by SEM and counting, lying broadly between 0.1 μm and 4 μm, preferably between 0.1 μm and 3 μm, and advantageously between 0.1 μm and 2 μm.

In the context of the present invention, binder means an inert inorganic matrix comprising amorphous materials such as silica, mixtures of silica and alumina and/or compounds such as clays. It is not outside the scope of the present invention if this matrix contains zeolitic crystalline materials other than zeolite LSX as defined previously in a quantity not exceeding 5% of the total weight of the aggregate.

The invention also relates to a method for preparing aggregates according to the invention, which comprises the following steps:

a) agglomeration of LSX zeolite crystals, with an agglomeration binder, which preferably contains at least 80% by weight of zeolitizable clay(s) (zeolitizable portion), and optionally a source of silica, followed by shaping, drying and calcination of the agglomerated powder, b) zeolitization of said zeolitizable portion of the binder by the action of a basic alkaline solution, c) replacement of at least 90% of the exchangeable sites of the product obtained in step b) by barium, followed by washing and drying of the product thus treated ("exchangeable sites of the aggregate" are understood to mean all the exchangeable sites of the zeolite LSX powder and those formed by the possible zeolitization of the binder), d) optionally, replacement of no more than 33% of the exchangeable sites of the product obtained in step c) by potassium, followed by washing and drying of the product thus treated, and e) optional activation of the product obtained, it being understood that the optional exchange with potassium (step d)) may be carried out before and/or after the exchange with barium (step c)).

Preferably, the preparation method according to the invention consists essentially of the steps a) to c)/then e), or a) to e), defined previously.

In step a), the agglomeration binder is preferably present in a proportion lower than or equal to 20% by weight of the total aggregate.

The size of the zeolite LSX crystals used in step a) and the zeolite LSX crystals contained in the aggregates is measured by observation and counting on the scanning electron microscope (SEM).

Observation by SEM also serves to confirm the presence of inert binder in the aggregates.

The zeolite LSX crystals having a mean number diameter lower than 4 μm used in the context of the present invention are considered as small crystals; the most commonly sold crystals of zeolite X have a general diameter above 7 μm.

At the agglomeration and shaping (step a)) can be carried out by any technique known to a person skilled in the art, such as extrusion, compaction, agglomeration.

The agglomeration binder essentially has the role of the shaping and agglomeration of the zeolite powders. Preferably, the binder is inert in the context of adsorption. The agglomeration binder used contains a zeolitizable portion, i.e. one or more zeolitizable clay(s), preferably 80% to 100% of the total weight of binder, and may also contain other mineral binders such as bentonite, attapulgite, sepiolite.

In the context of the present invention, zeolitizable clay means a clay or a mixture of clays which can be converted to zeolitic material by the action of a basic alkaline solution.

Zeolitizable clays generally belong to the family of kaolinite, halloysite, nacrites, dickites, kaolins and/or metakaolins, to which a silica source may be added. Kaolin is commonly used. The calcination that follows drying is carried out at a temperature generally between 500 and 600° C.

Furthermore, in step a), apart from the zeolite powder and agglomeration binder, additives may also be used, for example pore-forming agents and/or additives for facilitating the agglomeration and/or for improving the hardening of the aggregates formed.

The aggregates issuing from step a), whether in the form of beads, extrudates, generally have a mean number diameter of 0.4 to 2 mm, and in particular between 0.4 and 1.6 mm, more particularly between 0.4 and 0.8 mm.

In the present document, the term "mean number diameter" or "size" is employed for zeolite crystals and for zeolitic aggregates. The accuracy is about 3%.

On completion of step a), the finest aggregate particles can be removed by cyclone separation and/or sieving and/or the largest particles by sieving or crushing, in the case of extrudates for example.

The zeolite LSX powder used in step a) may be produced by the synthesis of zeolite crystals in NaKLSX form, but it is not outside the scope of the invention to use a powder having undergone one or more cationic exchanges, between the synthesis in NaKLSX form and its use in step a).

The zeolitization step b) achieves the conversion of at least 50% and preferably at least 70 to 82% by weight of the zeolitizable clay(s) contained in the binder of zeolitic material; it is found that zeolitization serves in particular to reinforce the mechanical strength of the aggregate zeolitic adsorbents.

Zeolitization can be carried out by immersion of the aggregate in a basic alkaline solution, generally aqueous, for example an aqueous solution of caustic soda and/or caustic potash, of which the concentration is preferably higher than 0.5 M. Said concentration is generally lower than 3 M, preferably lower than 2 M, advantageously lower than 1 M. The zeolitization preferably takes place hot (temperature above ambient temperature) typically at temperatures of about 80-100° C., in order to improve the kinetics of the process and to reduce the immersion times to less than hours, but it is not outside the scope of the invention to operate at lower temperatures and longer immersion times.

According to this procedure, the zeolitization of at least 50%, and preferably at least 70 to 82% by weight of the zeolitizable clay(s) contained in the binder is easily obtained. This is followed by a water washing followed by drying.

Step c) of exchange with barium of the cations of the zeolite takes place by contacting the aggregates issuing from step b) (or d)) with a barium salt, such as $BaCl_2$ in aqueous solution at a temperature of between ambient temperature and 100° C., and preferably between 80 and 100° C. To obtain a high barium exchange rate, i.e. higher than 90%, rapidly, it is preferable to operate with a large excess of barium with regard to the cations of the aggregate which are to be exchanged, typically such that the Ba/Al ratio is about 5 to 6, by proceeding with successive exchanges in order to reach the target minimum exchange rate of at least 90% and preferably at least 95%. Throughout the text, the exchange rates are calculated in equivalents and not in molarity.

The optional exchange with potassium (step d)) can be carried out before and/or after the exchange with barium (step c)) or simultaneously, using a solution containing the barium and potassium ions. As previously stated, it is also possible to agglomerate in step a) zeolite LSX powder already containing the potassium ions and eliminate (or not) step d).

The activation (step e)), the final step of the method for obtaining the adsorbents according to the invention, is intended to fix the moisture content and the ignition loss of the adsorbent within optimal limits. This is generally done by thermal activation which is preferably carried out between 200° C. and 300° C. for a certain length of time, typically from 1 to 6 hours, according to the desired moisture content and ignition loss, and depending on the intended use of the adsorbent.

The invention also relates to the uses of the zeolitic adsorbents described above as adsorption agents suitable for advantageously replacing the adsorption agents described in the literature based on zeolite X or based on zeolite LSX, exchanged with barium or exchanged with barium and potassium, and particularly to the uses listed below:
separation of $C_8$ aromatic isomers and particularly xylenes,
separation of sugars,
separation of polyhydric alcohols,
separation of isomers of substituted toluene such as nitrotoluene, diethyltoluene, toluenediamine,
separation of cresols,
separation of dichlorobenzenes.

The invention relates in particular to an improvement of the method for recovering paraxylene from aromatic $C_8$ isomer cuts by using, as a paraxylene adsorption agent, an aggregate zeolitic adsorbent according to the invention, used in liquid phase methods and also in gas phase methods.

The invention relates in particular to a method for producing high purity paraxylene from an aromatic hydrocarbon feedstock containing isomers with 8 carbon atoms comprising the following steps:
a) A step of contacting the feedstock with the bed of adsorbent according to the invention, under appropriate adsorption conditions, in order to preferably adsorb the paraxylene,
b) a step of contacting the adsorbent bed with a desorbent, which is preferably either toluene or paradiethylbenzene, under appropriate desorption conditions,
c) a step of withdrawing from the adsorbent bed a stream containing the desorbent and the least selectively adsorbed products of the feedstock,
d) a step of withdrawal from the adsorbent bed of a stream containing the desorbent and the paraxylene,
e) a separation of the stream issuing from step c) into a first stream containing the desorbent and a second stream containing the least selectively adsorbed products of the feedstock,
f) a separation of the stream issuing from step d) into a first stream containing the desorbent and the second stream containing the paraxylene in a purity higher than or equal to 75% and preferably higher than or equal to 99.7%.

The method may also optionally include the following step:
g) a step of crystallization in a crystallizer consisting of the crystallization of the paraxylene issuing from step f), in order to obtain on the one hand crystals of paraxylene impregnated with their mother liquor, and on the other a mother liquor which may partly, or completely, be recycled in a mixture with the fresh feedstock at the inlet of the simulated moving bed adsorption unit, h) a step of washing the crystals issuing from step g) after which the paraxylene is recovered in a purity of at least 99.7%, and preferably at least 99.8%.

The desired product can thus be separated by preparative adsorption liquid chromatography (in batches) advantageously in a simulated moving bed, that is, in simulated countercurrent or simulated cocurrent, and more particularly in simulated countercurrent.

The chromatographic separation in simulated moving bed in simulated countercurrent is well known in the prior art. In general, a simulated moving bed separation unit comprises at least one adsorption column containing a plurality of beds of an adsorbent, interconnected in a closed loop. The simulated moving bed separation unit comprises at least three chromatographic zones, and optionally four or five, each of these zones consisting of at least one bed or a portion of column and lying between two successive feed or withdrawal points. Typically, at least one feedstock to be fractionated and one desorbent (sometimes called eluant) are fed, and at least one raffinate and one extract are withdrawn. The feed and withdrawal points are modified over time, typically shifted toward the bottom of a bed and synchronously.

By definition, each of the operating zones is designated by a number:

Zone 1=zone of desorption of the desired product (contained in the extract) lying between the desorbent injection and the extract withdrawal;

Zone 2=zone of desorption of the compounds of the raffinate, lying between the extract withdrawal and the injection of the feedstock to be fractionated;

Zone 3=zone of adsorption of the desired product, lying between the feedstock injection and the raffinate withdrawal, and Zone 4 located between the raffinate withdrawal and the desorbent injection.

The operating conditions of an industrial adsorption unit of the simulated countercurrent type are generally as follows:
number of beds 6 to 30
number of zones at least 4
temperature 100 to 250° C., preferably 150 to 190° C.
pressure between the bubble point pressure of xylenes at the temperature of the process and 3 MPa
ratio of desorbent to feedstock flow rate 0.7 to 2.5 (for example 0.9 to 1.8 for a stand alone adsorption unit and 0.7 to 1.4 for an adsorption unit combined with a crystallization unit),
recycle rate from 2.5 to 12, preferably 3.5 to 6.

Reference can be made to the teaching of U.S. Pat. No. 2,985,589, U.S. Pat. No. 5,284,992 and U.S. Pat. No. 5,629,467.

The operating conditions of an industrial simulated cocurrent adsorption unit are generally the same as those operating in simulated countercurrent, with the exception of the recycle rate which is generally between 0.8 and 7. Reference can be made to U.S. Pat. No. 4,402,832 and U.S. Pat. No. 4,498,991.

The desorption solvent may be a desorbent having a boiling point lower than that of the feedstock, such as toluene, but also a desorbent of which the boiling point is higher than that of the feedstock, such as paradiethylbezene (PDEB). The selectivity of the adsorbents according to the invention for adsorbing the paraxylene contained in the $C_8$ aromatic cuts is optimal when their ignition loss measured at 900° C. is generally between 4.0 and 7.7%, and preferably between 4.7 and 6.7. Water and a little carbon dioxide are included in the ignition loss.

One of the techniques of choice for characterizing the adsorption of molecules in the liquid phase on a porous solid is to obtain a breakthrough. In his work "Principles of Adsorption and Adsorption Processes", Ruthven defines the technique of breakthrough curves as the analysis of the injection of an echelon of adsorbable constituents. This technique serves simultaneously to determine the properties of selectivity of the porous solid with regard to the molecules to be separated, and also the mass transfer properties.

The aggregates of the present invention have a mean diameter between 0.3 mm and 1.6 mm, and until today, there is no method available for characterizing the crush strength in a bed of aggregates having such a low mean diameter.

The Shell method series SMS1471-74 "Determination of Bulk Crushing Strength of Catalysts" Compression-Sieve Method associated with the "BCS Tester" apparatus sold by Vinci Technologies and which serves to determine the crush strength of a solid bed, is based on the following principle: a sample of 20 cm³ of aggregate adsorbents, previously oven-dried for at least 2 hours at 250° C., is placed in a metal cylinder having a known inside cross section. An increasing force is applied in steps to this sample via a piston.

The fines obtained at the various pressure plateaux are separated by sieving and weighed. The sieve used in the Shell standard method is a 425 µm sieve, which must be adapted for aggregates having a lower size than 1.6 mm, for which a 200 µm sieve is used. The crush strength of a bed is determined by the pressure in megapascals (MPa) at which the quantity of cumulative fines passing through the sieve amounts to 0.5% by weight of the sample.

This value is obtained by plotting a graph of the mass of fines obtained as a function of the force applied to the adsorbent bed and by interpolating at 0.5 by mass % of cumulative fines. The crush strength of the bed is typically between a few hundred kPa and a few tens of MPa, and is generally between 0.3 and 3.2 MPa.

The present invention is now described by means of the following examples, which are intended to illustrate certain embodiments of the invention, but without limiting the scope thereof as claimed in the appended claims.

Method for Synthesizing Zeolite LSX Powder
(Synthesis A)
Step a): Preparation of a Solution S1 of Sodium and Potassium Alluminate
A solution is prepared containing:
deionized water: 800 g
sodium hydroxide (99% pure): 420 g
potassium hydroxide (85% pure): 225 g.
This solution is heated to 115° C. and 240 g of aluminum hydroxide (gibbsite type) is added.
Step b): Preparation of a Solution S2 of Sodium Silicate
A solution is prepared containing:
deionized water: 620 g
sodium silicate: 710 g
Step c): Preparation of the Gel
In a 3 liter reactor equipped with an Archimedes screw stirrer, the solutions S1 and S2 are mixed using a defloculating turbine at 2000 rpm for 5 minutes to obtain a homogenous gel. This composition corresponds to the following stoichiometry:

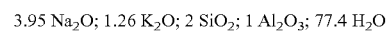
$$3.95\ Na_2O;\ 1.26\ K_2O;\ 2\ SiO_2;\ 1\ Al_2O_3;\ 77.4\ H_2O$$

After mixing the reagents and gelification, the gel then matures for 18 hours at 50° C., followed by crystallization for four hours at 95° C. The maturation and crystallization are carried out with stirring at a rate of 200 rpm.

The crystals obtained after filtration, washing and drying are identified by X-ray diffraction as faujasites. The chemical analysis of the solid gives a Si/Al ratio=1.01.

The microporous volume measured by the Dubinin method by nitrogen adsorption at 77K after pretreatment at 500° C. for 12 hours under vacuum is 0.308±0.003 cm³/g, for a crystallinity rate of 95.5%.

The size of the zeolite crystals is analyzed by scanning electron microscope. The mean size of the crystals is 2.6 µm.

EXAMPLE 1

Comparative, According to the General Teaching 840 g (expressed as calcined equivalent) of a zeolite LSX powder having a Si/Al ratio=1.01 obtained by the process described in European patent EP 0 486 384 or U.S. Pat. No. 5,173,462, is agglomerated by intimately mixing it with 160 g of Charentes kaolinite (expressed as calcined equivalent) with an adequate quantity of water to ensure the formation of aggregates by extrusion. The extrudates are dried, crushed in order to recover the aggregates having an equivalent diameter of 0.7 mm, and then calcined at 600° C. under nitrogen stream for 2 hours.

These aggregates are exchanged by means of a 0.5 M barium chloride solution at 95° C. in 4 steps. At each step, the ratio of solution volume to solid mass is 20 mL/g and the exchange is continued for 4 hours each time. Between each exchange, the solid is washed several times in order to remove the excess salt. It is then activated at a temperature of 200° C. for two hours under nitrogen stream.

The barium exchange rate is 94.7% and the ignition loss (measured at 900° C.) is 6.6%. The microporous volume measured by the Dubinin method by nitrogen adsorption at 77K after pretreatment at 500° C. for 12 hours under vacuum is 0.215 cm³/g.

The size of the zeolite crystals is analyzed by scanning electron microscope. The mean size of the crystals is 7 µm.

A breakthrough test (frontal chromatography) is then performed on these adsorbents to assess their effectiveness. The quantity of adsorbent used for this test is about 82 g.

The procedure for obtaining the breakthrough curves is as follows:
  filling of the column by the sieve and installation in the test bench,
  filling with the solvent at ambient temperature,
  progressive increase in adsorption temperature under solvent stream (5 cm³/min),
  solvent injection at 10 cm³/min when the adsorption temperature is reached,
  solvent/feedstock permutation to inject the feedstock (10 cm³/min),
  the injection of the feedstock is then maintained for a sufficient period to reach thermodynamic equilibrium,
  collection and analysis of the breakthrough effluent.

The pressure is sufficient so that the feedstock remains in the liquid phase, or 1 MPa. The adsorption temperature is 175° C.

The composition of feedstock is as follows:
  Paraxylene: 45 wt %
  Metaxylene: 45 wt %
  Iso-octane: 10 wt % (this is used as a tracer for estimating the nonselective volumes and is not involved in the separation).

The breakthrough results are given in Table 1 below.

The selectivity of paraxylene with regard to metaxylene is calculated by material balance.

TABLE 1

| Type of solid | PAF[1] at 900° C. | Temp[2] | Capacity[3] | Selectivity[4] $\alpha_{PX/MX}$ | Height of theoretical plate |
|---|---|---|---|---|---|
| BaLSX | 6.6% | 175° C. | 0.171 | 3.54 | 4.8 cm |

[1]PAF: Ignition loss
[2]Temp: Adsorption temperature
[3]The capacities expressed in cm³ of C8-aromatics adsorbed per gram of adsorbent
[4]PX: Paraxylene, MX: Metaxylene The mechanical strength is also measured by the method described in the specification of the invention. The pressure required to obtain 0.5% of fines is 2.40 MPa.

EXAMPLE 2

Comparative

In this example, an adsorbent of the prior art is prepared and tested: example 2 of U.S. Pat. No. 6,410,815 reproduced identically.

950 grams (calcined equivalent) of a zeolite LSX powder having a Si/Al ratio=1.01 obtained by the process described in European patent EP 0 486 384 or U.S. Pat. No. 5,173,462, is agglomerated with 170 g (calcined equivalent) of Charentes kaolinite, 6 g of carboxymethylcellulose and the adequate quantity of water to correctly extrude the paste obtained. The extrudates (aggregates) are then dried and calcined at a temperature of 600° C. for 2 hours under dry nitrogen stream. They are then crushed in order to reduce the equivalent diameter of the aggregates to 0.7 mm.

These aggregates are exchanged by means of a 0.5 M barium chloride solution at 95° C. in 4 steps. At each step, the ratio of solution volume to solid mass is 20 mL/g and the exchange is continued for 4 hours each time. Between each exchange, the solid is washed several times in order to remove the excess salt and then thermally activated at a temperature of 220° C. for two hours under nitrogen stream.

The barium exchange rate is 94.9% and the ignition loss is 5%. The microporous volume measured by the Dubinin method by nitrogen adsorption at 77K after pretreatment at 500° C. for 12 hours under vacuum is 0.208 cm³/g.

The size of the zeolite crystals is analyzed by scanning electron microscope. The mean size of the crystals is 7 µm.

A breakthrough test (frontal chromatography) is then performed on these adsorbents to assess their effectiveness. The quantity of adsorbent used for this test is about 80 g. The procedure and the feedstock composition are identical to those of example 1.

The breakthrough results are given in Table 2 below.

The selectivity of paraxylene with regard to metaxylene is calculated by material balance.

TABLE 2

| Type of solid | PAF[1] at 900° C. | Temp[2] | Capacity[3] | Selectivity[4] $\alpha_{PX/MX}$ | Height of theoretical plate |
|---|---|---|---|---|---|
| BaLSX | 5.0% | 175° C. | 0.172 | 3.40 | 11.5 cm |

[1]PAF: Ignition loss
[2]Temp: Adsorption temperature
[3]The capacities expressed in cm³ of C8-aromatics adsorbed per gram of adsorbent TABLE 2-continued

| Type of solid | PAF[1] at 900° C. | Temp[2] | Capacity[3] | Selectivity[4] $\alpha_{PX/MX}$ | Height of theoretical plate |
|---|---|---|---|---|---|

[4]PX: Paraxylene, MX: Metaxylene

The method of measuring selectivity by the breakthrough test is different from the one measured by the static test, in a test method used in patent U.S. Pat. No. 6,410,815. This explains why the selectivity of paraxylene with regard to metaxylene calculated in this example is different from the one reported in Example 2 of U.S. Pat. No. 6,410,815, although the adsorbent is identical.

However, for comparison, the selectivity measurement by static test was performed under the same conditions as those described in U.S. Pat. No. 6,410,815 and yields similar results to those obtained in said patent.

The mechanical strength is also measured by the method described in the specification of the invention. The pressure required to obtain 0.5% of fines is 2.20 MPa.

EXAMPLE 3

Comparative 840 g (expressed as calcined equivalent) of zeolite LSX powder obtained according to the synthesis example A described above, are agglomerated by mixing it intimately with 160 g of kaolin (expressed as calcined equivalent) with an adequate quantity of water to ensure the formation of aggregates by extrusion. The extrudates are dried, crushed in order to recover the aggregates having an equivalent diameter of 0.7 mm, and then calcined at 600° C. under nitrogen stream for 2 hours.

The barium exchange is carried out under identical operating conditions to those of example 1, with the exception of the concentration of the $BaCl_2$ solution, which is 0.7 M, followed by washing and then drying at 80° C. for 2 hours, and finally, activation at 200° C. for 2 hours under nitrogen stream.

The barium exchange rate is 98% and the ignition loss (measured at 900° C.) is 6.3%. The microporous volume measured by the Dubinin method by nitrogen adsorption at 77K after pretreatment at 500° C. for 12 hours under vacuum is 0.205 cm$^3$/g.

The size of the zeolite crystals is analyzed by scanning electron microscope. The mean size of the crystals is 2.6 μm.

A breakthrough test (frontal chromatography) is then performed on these aggregate zeolitic adsorbents to assess their effectiveness. The quantity of adsorbent used for this test is about 82 g.

The procedure and the feedstock composition are identical to those of the example 1. The breakthrough results are given in Table 3 below.

The selectivity of paraxylene with regard to metaxylene is calculated by material balance.

TABLE 3

| Type of solid | PAF[1] at 900° C. | Temp[2] | Capacity[3] | Selectivity[4] $\alpha_{PX/MX}$ | Height of theoretical plate |
|---|---|---|---|---|---|
| BaLSX | 6.3% | 175° C. | 0.155 | 4.03 | 2.54 cm |

[1]PAF: Ignition loss
[2]Temp: Adsorption temperature

TABLE 3-continued

| Type of solid | PAF[1] at 900° C. | Temp[2] | Capacity[3] | Selectivity[4] $\alpha_{PX/MX}$ | Height of theoretical plate |
|---|---|---|---|---|---|

[3]The capacities expressed in cm$^3$ of C8-aromatics adsorbed per gram of adsorbent
[4]PX: Paraxylene, MX: Metaxylene The mechanical strength is also measured by the method described in the specification of the invention. The pressure required to obtain 0.5% of fines is 1.90 MPa.

COMPARATIVE EXAMPLE 4

In this example, an adsorbent of the prior art is prepared and tested.

840 g (expressed as calcined equivalent) of a zeolite LSX powder having a Si/Al ratio=1.01 obtained by the process described in European patent EP 0 486 384 or U.S. Pat. No. 5,173,462, is agglomerated by intimately mixing it with 160 g of Charentes kaolinite (expressed as calcined equivalent) with an adequate quantity of water to operate by extrusion. The extrudates are dried, crushed in order to recover the aggregates having an equivalent diameter of 0.7 mm, and then calcined at 600° C. under nitrogen stream for 2 hours.

200 g of aggregates thus obtained are placed in a glass reactor provided with a double jacket regulated at a temperature of 95±1° C. and 700 mL of an aqueous solution of caustic soda having a concentration of 220 g/L is added, and the reaction medium is left with stirring for 3 hours. The granules are then washed in successive operations followed by drainage of the reactor. The effectiveness of the washing is verified by measuring the final pH of the wash water, which must be between 10 and 10.5.

Barium exchange is then carried out under the identical operating conditions as those in example 1 followed by washing and then drying at 80° C. for two hours, and finally activation at 200° C. for 2 hours under nitrogen stream. The barium exchange rate of this adsorbent is 96% and the ignition loss is 6.9%. The microporous volume measured by the Dubinin method by nitrogen adsorption at 77K after pretreatment at 500° C. for 12 hours under vacuum is 0.242 cm$^3$/g.

The size of the zeolite crystals is analyzed by scanning electron microscope. The mean size of the crystals is 7 μm.

A breakthrough test (frontal chromatography) is then performed on these aggregate zeolitic adsorbents to assess their effectiveness. The quantity of adsorbent used for this test is about 82 g.

The procedure and the feedstock composition are identical to those of the example 1. The breakthrough results are given in Table 4 below.

The selectivity of paraxylene with regard to metaxylene is calculated by material balance.

TABLE 4

| Type of solid | PAF[1] at 900° C. | Temp[2] | Capacity[3] | Selectivity[4] $\alpha_{PX/MX}$ | Height of theoretical plate |
|---|---|---|---|---|---|
| BaLSX | 6.9% | 175° C. | 0.191 | 3.57 | 3.62 cm |

[1]PAF: Ignition loss
[2]Temp: Adsorption temperature
[3]The capacities expressed in cm$^3$ of C8-aromatics adsorbed per gram of adsorbent
[4]PX: Paraxylene, MX: Metaxylene The mechanical strength is also measured by the method described in the specification of the invention. The pressure required to obtain 0.5% of fines is 2.70 MPa.

EXAMPLE 5

Comparative

In this example, an adsorbent of the prior art is prepared and tested: example 3 of U.S. Pat. No. 6,410,815, reproduced identically.

950 grams of a zeolite LSX having a Si/Al ratio=1.01, obtained by the process described in European patent EP 0 486 384 or U.S. Pat. No. 5,173,462, is agglomerated with 170 g of Charentes kaolinite, 6 g of carboxymethylcellulose and the adequate quantity of water. Extrusion is carried out. The extrudates are dried, calcined at a temperature of 600° C. for 2 hours under dry nitrogen stream, and then crushed in order to reduce their equivalent diameter to 0.7 mm.

200 g of these aggregates are then immersed in 340 mL of a 220 g/L caustic soda solution for three hours at 95° C. They are washed with water four times in succession.

The solid is then exchanged with barium under the same conditions as those of example 2, followed by washing and then drying at 80° C. for two hours, and finally activation at 200° C. for 2 hours under nitrogen stream.

The barium exchange rate of this adsorbent is 96.5% and the ignition loss is 6.6%. The microporous volume measured by the Dubinin method by nitrogen adsorption at 77K after pretreatment at 500° C. for 12 hours under vacuum is 0.237 $cm^3/g$.

The size of the zeolite crystals is analyzed by scanning electron microscope. The mean size of the crystals is 7 μm.

A breakthrough test (frontal chromatography) is then performed on these adsorbents to assess their effectiveness. The quantity of adsorbent used for this test is about 82 g.

The procedure and the feedstock composition are identical to those of the example 1.

The breakthrough results are given in Table 5 below.

TABLE 5

| Type of solid | PAF[1] at 900° C. | Temp[2] | Capacity[3] | Selectivity[4] $\alpha_{PX/MX}$ | Height of theoretical plate |
|---|---|---|---|---|---|
| BaLSX | 6.6% | 175° C. | 0.189 | 3.61 | 4.80 cm |

[1]PAF: Ignition loss
[2]Temp: Adsorption temperature
[3]The capacities expressed in $cm^3$ of C8-aromatics adsorbed per gram of adsorbent
[4]PX: Paraxylene, MX: Metaxylene The method for measuring selectivity by the breakthrough test is different from the one measured by the static test, in a test method used in patent U.S. Pat. No. 6,410,815. This explains why the selectivity of paraxylene with regard to metaxylene calculated in this example is different from the one reported in Example 3 of U.S. Pat. No. 6,410,815, although the adsorbent is identical.

However, for comparison, the selectivity measurement by static test was performed under the same conditions as those described in patent U.S. Pat. No. 6,410,815 and yields similar results to those obtained in said patent.

The mechanical strength is also measured by the method described in the specification of the invention. The pressure required to obtain 0.5% of fines is 2.50 MPa.

EXAMPLE 6

According to the Invention 840 g (expressed as calcined equivalent) of zeolite LSX powder obtained according to the synthesis example A described above, is intimately mixed and agglomerated with 160 g of kaolin (expressed as calcined equivalent) with an adequate quantity of water to operate by extrusion. The extrudates are dried, crushed in order to recover the grains having an equivalent diameter of 0.7 mm, and then calcined at 600° C. under nitrogen stream for 2 hours.

200 g of granules thus obtained are placed in a glass reactor provided with a double jacket regulated at a temperature of 95±1° C. and 700 mL of an aqueous solution of caustic soda having a concentration of 220 g/L is added, and the reaction medium is left with stirring for 3 hours. The granules are then washed in successive operations followed by drainage of the reactor.

The effectiveness of the washing is verified by measuring the final pH of the wash water, which must be between 10 and 10.5.

Barium exchange is then carried out under the identical operating conditions as those in example 1 followed by washing and then drying at 80° C. for two hours, and finally activation at 200° C. for 2 hours under nitrogen stream.

The barium exchange rate of this adsorbent is 97% and the ignition loss is 6.5%. The microporous volume measured by the Dubinin method by nitrogen adsorption at 77K after pretreatment at 500° C. for 12 hours under vacuum is 0.235 $cm^3/g$.

The size of the zeolite crystals is analyzed by scanning electron microscope. The mean size of the crystals is 2.6 μm.

A breakthrough test (frontal chromatography) is then performed on these adsorbents to assess their effectiveness. The quantity of adsorbent used for this test is about 82 g.

The procedure and the feedstock composition are identical to those of the example 1.

The breakthrough results are given in Table 6 below.

The selectivity of paraxylene with regard to metaxylene is calculated by material balance.

TABLE 6

| Type of solid | PAF[1] at 900° C. | Temp[2] | Capacity[3] | Selectivity[4] $\alpha_{PX/MX}$ | Height of theoretical plate |
|---|---|---|---|---|---|
| BaLSX | 6.5% | 175° C. | 0.178 | 3.98 | 2.20 |

[1]PAF: Ignition loss
[2]Temp: Adsorption temperature
[3]The capacities expressed in $cm^3$ of C8-aromatics adsorbed per gram of adsorbent
[4]PX: Paraxylene, MX: Metaxylene The mechanical strength is also measured by the method described in the specification of the invention. The pressure required to obtain 0.5% of fines is 2.70 MPa.

EXAMPLE 7

Comparative 840 g (expressed as calcined equivalent) of zeolite LSX powder obtained according to the synthesis example A described above, is intimately mixed and agglomerated with 52 g of kaolin (expressed as calcined equivalent) with an adequate quantity of water to operate by extrusion. The extrudates are dried, crushed in order to recover the grains having an equivalent diameter of 0.7 mm, and then calcined at 600° C. under nitrogen stream for 2 hours.

The barium exchange is carried out under the identical operating conditions as those in example 1 followed by washing and then drying at 80° C. for two hours, and finally activation at 200° C. for 2 hours under nitrogen stream.

The barium exchange rate of this adsorbent is 97.2% and the ignition loss is 6.4%. The microporous volume measured by the Dubinin method by nitrogen adsorption at 77K after pretreatment at 500° C. for 12 hours under vacuum is 0.232 cm³/g.

The size of the zeolite crystals is analyzed by scanning electron microscope. The mean size of the crystals is 2.6 μm.

A breakthrough test (frontal chromatography) is then performed on these adsorbents to assess their effectiveness. The quantity of adsorbent used for this test is about 82 g.

The procedure and the feedstock composition are identical to those of the example 1.

The breakthrough results are given in Table 7 below.

The selectivity of paraxylene with regard to metaxylene is calculated by material balance.

TABLE 7

| Type of solid | PAF[1] at 900° C. | Temp[2] | Capacity[3] | Selectivity[4] $\alpha_{PX/MX}$ | Height of theoretical plate |
|---|---|---|---|---|---|
| BaLSX | 6.4% | 175° C. | 0.176 | 4.00 | 0.20 cm |

[1]PAF: Ignition loss
[2]Temp: Adsorption temperature
[3]The capacities expressed in cm³ of C8-aromatics adsorbed per gram of adsorbent
[4]PX: Paraxylene, MX: Metaxylene The mechanical strength is also measured by the method described in the specification of the invention. The pressure required to obtain 0.5% of fines is 0.20 MPa.

It is observed that at identical adsorption capacity, an aggregate which has not been prepared by the method described in the present invention has good selectivity, good mass transfer, but has no mechanical strength.

EXAMPLE 8

Comparative 950 grams of a zeolite LSX having a Si/Al ratio=1.01, obtained by the process described in European patent EP 0 486 384 or U.S. Pat. No. 5,173,462, having a crystal size of 7 μm with 170 g of kaolin, and the adequate quantity of water. Extrusion is carried out. The extrudates are dried, calcined at a temperature of 600° C. for 2 hours under dry nitrogen stream, and then crushed in order to reduce their equivalent diameter to 0.7 mm.

200 g of these aggregates are then immersed in 340 mL of a 220 g/L caustic soda solution for 3 hours at 95° C. They are washed with water four times in succession.

Intensive exchange with potassium is then carried out with a 1 M KCl solution at 25° C. in 4 successive steps.

At each step, the ratio of solution volume to solid mass is 20 mL/g and the exchange is continued for 4 hours each time. Between each exchange, the solid is washed several times in order to remove the excess salt. The product obtained has a potassium exchange rate of 97.5%.

The aggregate is then subjected to 2 barium exchange operations identical to those described in example 1.

After all these operations, the solid is finally activated at a temperature of 200° C. for 2 hours under nitrogen stream.

It has the following properties: barium exchange rate 74.3%, potassium exchange rate 24%.

The microporous volume measured by the Dubinin method by nitrogen adsorption at 77K after pretreatment at 500° C. for 12 hours under vacuum is 0.250 cm³/g and an ignition loss at 900° C. of 6.6%.

EXAMPLE 9

Adsorbent According to the Invention

Aggregate samples are prepared as described in example 8, but using zeolite LSX powder obtained according to synthesis in example A described above.

Before the barium exchange, a potassium exchange is carried out by placing the above granules in contact with an aqueous solution of KCl following the same experimental procedure as in example 8.

The aggregate is then subjected to 2 barium exchange operations identical to those described in example 8.

After all these operations, the solid is finally activated at a temperature of 200° C. for 2 hours under nitrogen stream.

It has the following properties: barium exchange rate 75.5%, potassium exchange rate: 23%.

The microporous volume measured by the Dubinin method by nitrogen adsorption at 77K after pretreatment at 500° C. for 12 hours under vacuum is 0.244 cm³/g and an ignition loss at 900° C. of 6.4%.

The invention claimed is:

1. An aggregate zeolitic adsorbent comprising an inert binder and LSX zeolite crystals having a mean number diameter of between 0.1 μm and 4 μm, a Si/Al atomic ratio=1.00±0.05, wherein at least 90% of the exchangeable cationic sites are occupied either by barium ions or by barium ions and potassium ions, wherein the mechanical strength of the adsorbent measured by the Shell series SMS1417-74 method is greater than or equal to 2 MPa.

2. The aggregate zeolitic adsorbent as claimed in claim 1, wherein the Dubinin volume is greater than or equal to 0.200 cm³/g.

3. The aggregate zeolitic adsorbent as claimed in claim 1, wherein the exchangeable sites occupied by potassium may account for up to ⅓ of the exchangeable sites occupied by the barium plus potassium ions, and whereof an optional complement is provided by alkali or alkaline-earth ions other than barium and potassium.

4. The aggregate zeolitic adsorbent as claimed in claim 1, wherein the binder is inert to adsorption in a proportion of less than or equal to 20% by weight of the total mass of aggregate.

5. The aggregate zeolitic adsorbent as claimed in claim 1, having a size distribution giving a mean diameter of between 0.3 mm and 1.6 mm.

6. The aggregate zeolitic adsorbent as claimed in claim 1, wherein the total exchange rate of barium alone or of barium plus potassium is greater than or equal to 95%.

7. The aggregate zeolitic adsorbent as claimed in claim 1, wherein the ignition loss measured at 900° C. is between 4.0 and 7.7%.

8. The aggregate zeolitic adsorbent as claimed in claim 1, wherein the mean number diameter of the crystals is between 0.1 μm and 4 μm.

9. A method for preparing an aggregate zeolitic adsorbent as claimed in claim 1, comprising the following steps:
   a) agglomeration of LSX zeolite crystals, with an agglomeration binder, and optionally a source of silica, followed by shaping, drying and calcination of the agglomerated powder, the number average diameter of the LSX zeolite crystals being between 0.1 μm and 4 μm,
   b) zeolitization of said zeolitizable portion of the binder by the action of a basic alkaline solution,
   c) replacement of at least 90% of the exchangeable sites of the product obtained in step b) by barium, followed by washing and drying of the product thus treated, d) optionally, replacement of no more than 33% of the exchangeable sites of the product obtained in step c) by potassium, followed by washing and drying of the product thus treated, and e) optional activation of the product obtained, it being understood that the optional exchange with potassium (step d)) may be carried out before and/or after the exchange with barium (step c)).

10. The method as claimed in claim 9, in which, in step a), the agglomeration binder is in a proportion lower than or equal to 20% by weight of the total aggregate.

11. The method as claimed in claim 9, in which the activation in step e) is a thermal activation, carried out at a temperature between 200° C. and 300° C.

12. The method as claimed in claim 9, in which the basic alkaline solution in step b) has a concentration of at least 0.5 M.

13. An aggregate zeolitic adsorbent obtained by the method as claimed in claim 9.

14. The aggregate zeolitic adsorbent as claimed in claim 1, wherein the Dubinin volume is greater than or equal to 0.220 cm$^3$/g.

15. The aggregate zeolitic adsorbent as claimed in claim 1, wherein the Dubinin volume is greater than or equal to 0.225 cm$^3$/g.

16. The aggregate zeolitic adsorbent as claimed in claim 1, comprising a binder that is inert to adsorption in a proportion of less than or equal to 15% by weight, of the total mass of aggregate.

17. The aggregate zeolitic adsorbent as claimed in claim 1, wherein the ignition loss measured at 900° C. is broadly between 4.7 and 6.7%.

18. The aggregate zeolitic adsorbent as claimed in claim 1, wherein the mean number diameter of the crystals is between 0.1 μm and 3 μm.

19. The aggregate zeolitic adsorbent as claimed in claim 1, wherein the mean number diameter of the crystals is between 0.1 μm and 2 μm.

20. A method according to claim 9, wherein the agglomeration binder contains at least 80% by weight of zeolitizable clay(s) (zeolitizable portion).

21. A method according to claim 9, wherein the number average diameter of the LSX zeolite crystals is between 0.1 μm and 3 μm.

22. A method according to claim 9, wherein the number average diameter of the LSX zeolite crystals is between 0.1 μm and 2 μm.

23. A method for producing high purity paraxylene from an aromatic hydrocarbon feedstock containing isomers with 8 carbon atoms comprising the following steps:

a) a step of contacting the feedstock with a bed of the adsorbent as defined in claim 1, b) a step of contacting the adsorbent bed with a desorbent, c) a step of withdrawing from the adsorbent bed a stream containing the desorbent and the least selectively adsorbed products of the feedstock, d) a step of withdrawal from the adsorbent bed of a stream containing the desorbent and the paraxylene, e) a separation of the stream issuing from step c) into a first stream containing the desorbent and a second stream containing the least selectively adsorbed products of the feedstock, f) a separation of the stream issuing from step d) into a first stream containing the desorbent and the second stream containing the paraxylene in a purity higher than or equal to 75%.

24. The method as claimed in claim 23, which is carried out in the liquid phase.

25. The method as claimed in claim 23, which is carried out in the gas phase.

26. The method as claimed in claim 23, where the bed is of the simulated moving bed type.

27. The method as claimed in claim 23, where the bed is of the simulated countercurrent type.

28. The method as claimed in claim 23, where the bed is of the simulated cocurrent type.

29. The method as claimed in claim 23, in which the desorbent is selected from toluene and paradiethylbenzene.

* * * * *